United States Patent
Norstrem

(10) Patent No.: US 10,842,660 B1
(45) Date of Patent: Nov. 24, 2020

(54) LUMBOSACRAL SPINAL SUPPORT, COMPRESSION AND TREATMENT ARTICLE

(71) Applicant: Core Products International, Inc., Osceola, WI (US)

(72) Inventor: Paul R. Norstrem, Dresser, WI (US)

(73) Assignee: Core Products International, Inc., Osceola, WI (US)

( * ) Notice: Subject to any disclaimer, the term of this patent is extended or adjusted under 35 U.S.C. 154(b) by 762 days.

(21) Appl. No.: 14/920,406

(22) Filed: Oct. 22, 2015

Related U.S. Application Data

(60) Provisional application No. 62/067,145, filed on Oct. 22, 2014.

(51) Int. Cl.
- *A61F 5/00* (2006.01)
- *A61F 5/02* (2006.01)
- *A61N 1/04* (2006.01)
- *A61N 1/36* (2006.01)

(52) U.S. Cl.
CPC ............ *A61F 5/028* (2013.01); *A61N 1/0456* (2013.01); *A61N 1/36021* (2013.01)

(58) Field of Classification Search
CPC ... A61N 1/0456; A61N 1/36021; A61F 5/028; A61F 5/03
USPC ....................................... 602/19, 2
See application file for complete search history.

(56) References Cited

U.S. PATENT DOCUMENTS

| | | | | |
|---|---|---|---|---|
| 3,096,760 A * | 7/1963 | Nelkin | ............ | A61F 5/028 128/95.1 |
| 4,475,543 A * | 10/1984 | Brooks | ............ | A61L 15/07 602/19 |
| 5,179,942 A * | 1/1993 | Drulias | ............ | A61F 5/028 128/101.1 |
| 5,334,134 A * | 8/1994 | Saunders | ........... | A41D 13/0525 128/100.1 |
| 5,445,601 A * | 8/1995 | Harlow | ............ | A61F 5/028 128/845 |
| 5,785,671 A * | 7/1998 | Striano | ............ | A61F 5/028 128/96.1 |
| 6,099,490 A * | 8/2000 | Turtzo | ............ | A61F 5/028 2/311 |
| 6,109,655 A | 8/2000 | Wheeler | | |
| 8,956,315 B2 * | 2/2015 | Garth | ............ | A61F 5/028 602/19 |

(Continued)

FOREIGN PATENT DOCUMENTS

| | | | | |
|---|---|---|---|---|
| EP | 1452155 A2 * | 9/2004 | ........... | A61F 5/028 |
| FR | 2992168 A1 * | 12/2013 | ........... | A61F 5/0106 |

*Primary Examiner* — Kim M Lewis
(74) *Attorney, Agent, or Firm* — Schwegman Lundberg & Woessner, P.A.

(57) ABSTRACT

An improved lumbosacral wrap is generally provided. In an example, a lumbosacral wrap can include a lumbosacral panel, first and second bilateral panels, and a posterior pad. In certain examples, the lumbosacral wrap can include a wireless transcutaneous electrical nerve stimulation (TENS) device selectively supported by the lumbosacral panel or the posterior pad. In certain examples, the wireless TENS device is receivable within a cavity of a user engaging surface of the posterior pad in furtherance of supplementing support and compression of a lumbosacral spine with mobile treatment.

20 Claims, 4 Drawing Sheets

(56) References Cited

U.S. PATENT DOCUMENTS

| | | | |
|---|---|---|---|
| 2006/0122547 A1* | 6/2006 | Stewart, III | A61F 5/028 602/19 |
| 2009/0254015 A1* | 10/2009 | Segal | A61F 5/024 602/19 |
| 2010/0211122 A1* | 8/2010 | Hensley | A61F 7/02 607/3 |
| 2014/0309571 A1* | 10/2014 | Kilbey | A61F 5/028 602/19 |
| 2015/0025427 A1* | 1/2015 | Chen | A61F 5/028 602/2 |
| 2015/0141892 A1* | 5/2015 | Ingimundarson | A61F 5/028 602/19 |
| 2016/0096027 A1* | 4/2016 | Asseo | A61N 1/37223 607/60 |

* cited by examiner

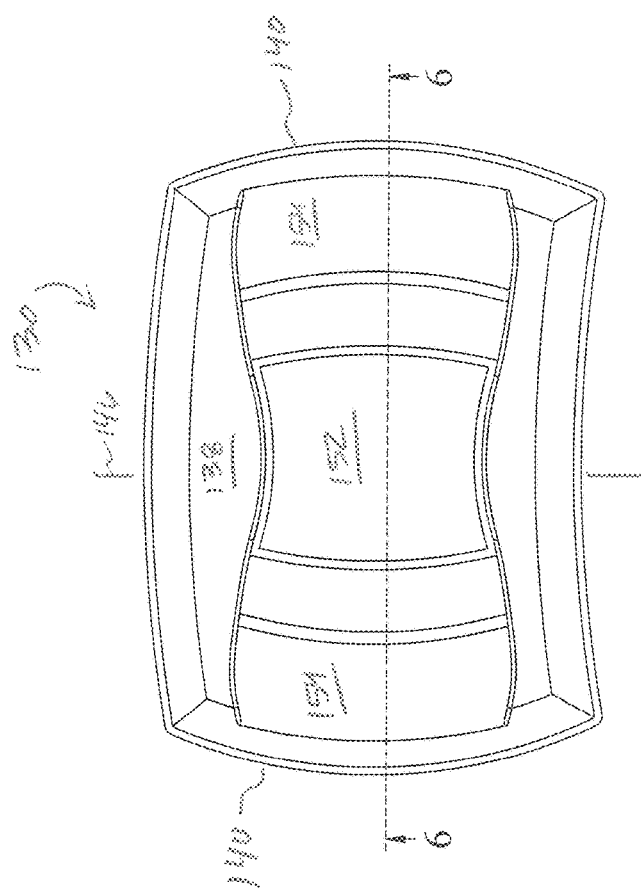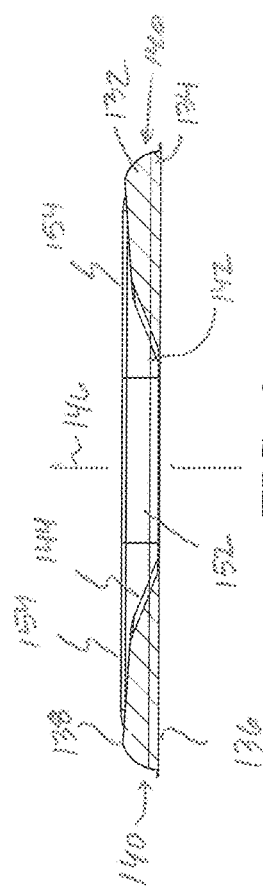

LUMBOSACRAL SPINAL SUPPORT, COMPRESSION AND TREATMENT ARTICLE

This is a United States national patent application filed pursuant to 35 USC § 111(a) claiming priority under 35 USC § 120 of/to U.S. Pat. Appl. Ser. No. 62/067,145 filed Oct. 22, 2014 and entitled LUMBAR SUPPORT & TREATMENT ARTICLE, the disclosure of which is hereby incorporated by reference in its entirety.

TECHNICAL FIELD

The present invention generally relates to spinal support structures or devices, more particularly, to a non-indwelling structure or device for the support, compression and/or treatment of a lumbosacral region of the spine, more particularly still and advantageously, to a lumbosacral support and compression wrap or belt adapted to deliver transcutaneous electrical nerve stimulation (TENS), and more particularly yet, to a lumbosacral spinal support and compression wrap which is adapted, or has a portion adapted, for selective receipt and retention of a wireless TENS unit.

BACKGROUND OF THE INVENTION

More than thirty bones, i.e., vertebrae, combine to form the spinal column, a/k/a, the spine, which houses the spinal cord. Spacing between the vertebrae are maintained by intervertebral cartilage discs which allow for spine flexure and general cushioning of the spinal structure and its components.

The spine comprises four regions. First are the seven cervical or neck vertebrae, generally designated C1-C7; second, the twelve thoracic or upper back vertebrae, generally designated T1-T12; third, the five lumbar or lower back vertebrae, generally designated L1-L5; and, fourth, the sacrum and coccyx, a/k/a "tail bone," which are fused together and form the base of the spine.

Low back pain is commonly characterized as acute, i.e., short term, or chronic, i.e., three months or more of persistent pain. As to the former, origins of short term low back pain are typically mechanical in nature, the result of trauma to the lower back, i.e., a stress upon spinal bones or tissue, or a disorder such as arthritis. Recurring lower back pain resulting from improper body mechanics or other non-traumatic causes is oftentimes believed preventable.

A wide variety of well known non-invasive conventional interventions are available for symptomatic relief and/or treatment, for example and without limitation, application of compresses, bed rest, exercise, medications, and spinal manipulation. Moreover, less conventional approaches to symptomatic relief/treatment include, but are not limited to acupuncture, biofeedback, interventional therapy, traction, transcutaneous electrical nerve stimulation (TENS), and ultrasound.

In furtherance of the relief and prevention of lower back pain, numerous low back support devices, commonly in the form of a wrap or "belt," are known and intended to properly support the lumbosacral spine, see e.g., the CorFit® Advantage AP from Applicant/Assignee Core Products International, Inc., Wisconsin, USA, see also previously pending U.S. patent application Ser. No. 13/290,654 filed Nov. 7, 2011 incorporated herein by reference in its entirety. While direct support of the spine and its musculature can be effective, it is believed especially advantageous to support the spine in combination with at least portions of the "core," i.e., the musculature of the lumbar spine, abdominals, and hips. Generally, it is believed advantageous to provide an upward and inward support of the abdominal region in furtherance of low back support.

While lower back core support and stability are critical, hybrid functionality remains a sought after goal. In particular, it is believed both desirable and advantageous to provide a device or article for lumbosacral spinal support, select compression, and select stimulation of the soft tissue of the lumbosacral spine, further still, to provide a wearable combination support, compression and stimulation/treatment article that permits a distressed user self-help with heretofore unavailable convenience.

SUMMARY OF THE INVENTION

An improved lumbosacral wrap is generally provided. The wrap includes a lumbosacral panel, first and second bilateral panels, a posterior pad, and a wireless transcutaneous electrical nerve stimulation (TENS) device selectively supported by the lumbosacral panel or the posterior pad. The lumbosacral panel is characterized by opposing longitudinal margins and opposing lateral margins. The first bilateral panel extends from a first margin of the opposing lateral margins of the lumbosacral panel. The second bilateral panel extends from a second margin of the opposing lateral margins of the lumbosacral panel. The posterior pad is supportable by the lumbosacral panel intermediate the opposing lateral margins thereof, the pad having a panel engaging surface, a user engaging surface, and opposing sides, the user engaging surface of the pad characterized by a cavity or the like extending between the opposing sides of the posterior pad. The wireless TENS device is receiveable with the cavity of the user engaging surface of the pad in furtherance of supplementing support and compression of a lumbosacral spine with mobile treatment. More specific features and advantages obtained in view of those features will become apparent with reference to the drawing figures and DETAILED DESCRIPTION OF THE INVENTION.

BRIEF DESCRIPTION OF THE DRAWINGS

FIG. 5 depicts an alternate posterior pad, front elevation, equipped with the wireless TENS unit of FIG. 3; and, FIG. 6 depicts a sectional view of the posterior pad of FIG. 5 about line 6-6 thereof, namely, through a horizontal centerline of the wireless TENS unit supported thereby.

DESCRIPTION OF PREFERRED EMBODIMENTS

The subject lumbosacral spinal support wrap or belt is advantageously, but not necessarily, characterized by a posterior panel having an interior/user surface adapted to selectively receive and retain a wireless TENS unit. While support belts and wireless TENS units are well known, a hybrid functional combination of support, support/selective compression of lower back structures, suppression of the transmission of nerve pain (i.e., Gate Control Theory), and reduction of pain sensitivity (i.e., Opiate Release Theory) have yet to be offered in the context of a wrap, belt, etc. which is characterized by a heretofore unseen ease of use.

Figure 1:
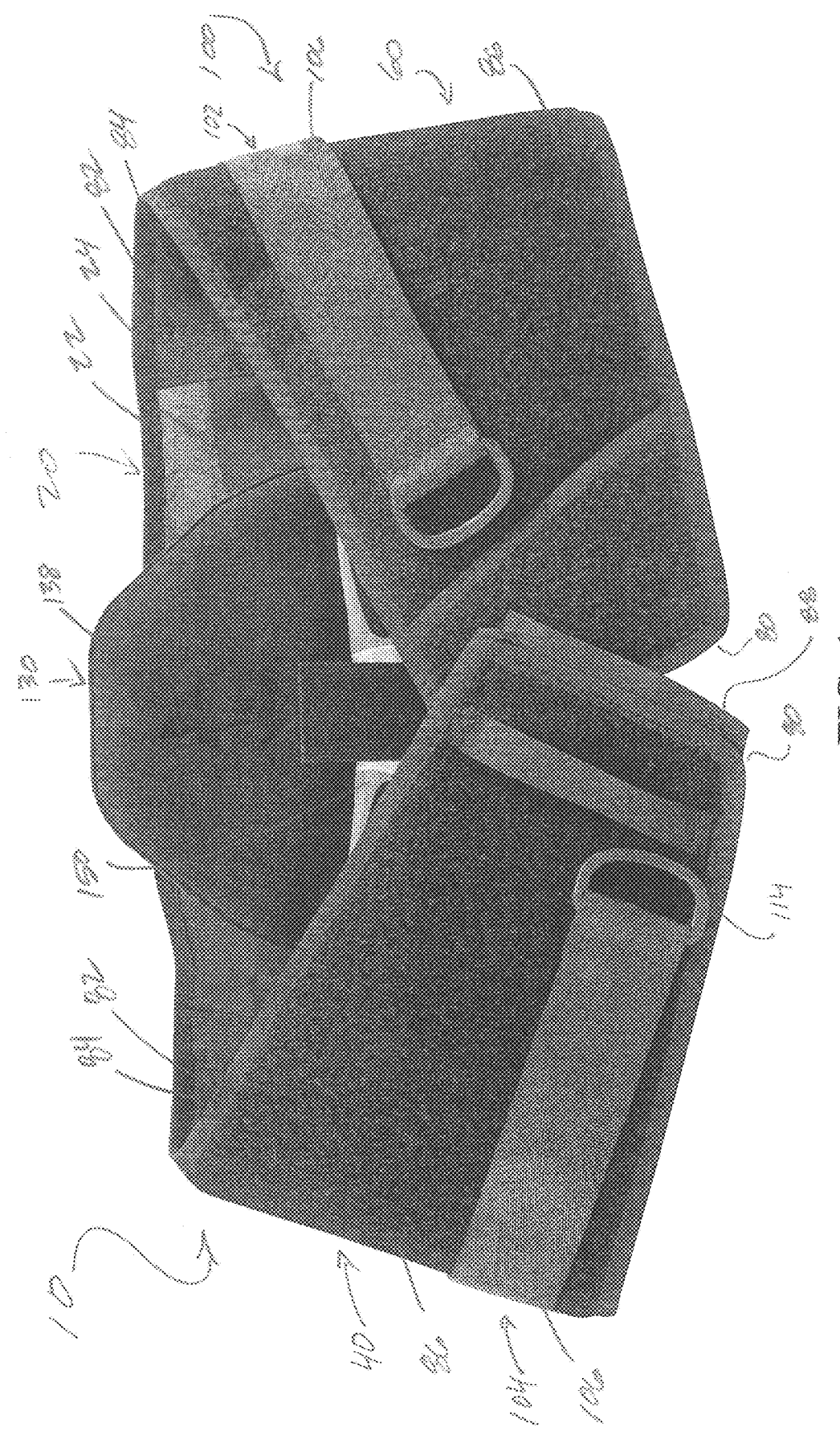
FIG. 1. depicts a preferred non-limiting lumbosacral wrap, front elevation, opposing bilateral panels partially united in a partial wrap condition.
Figure 2:
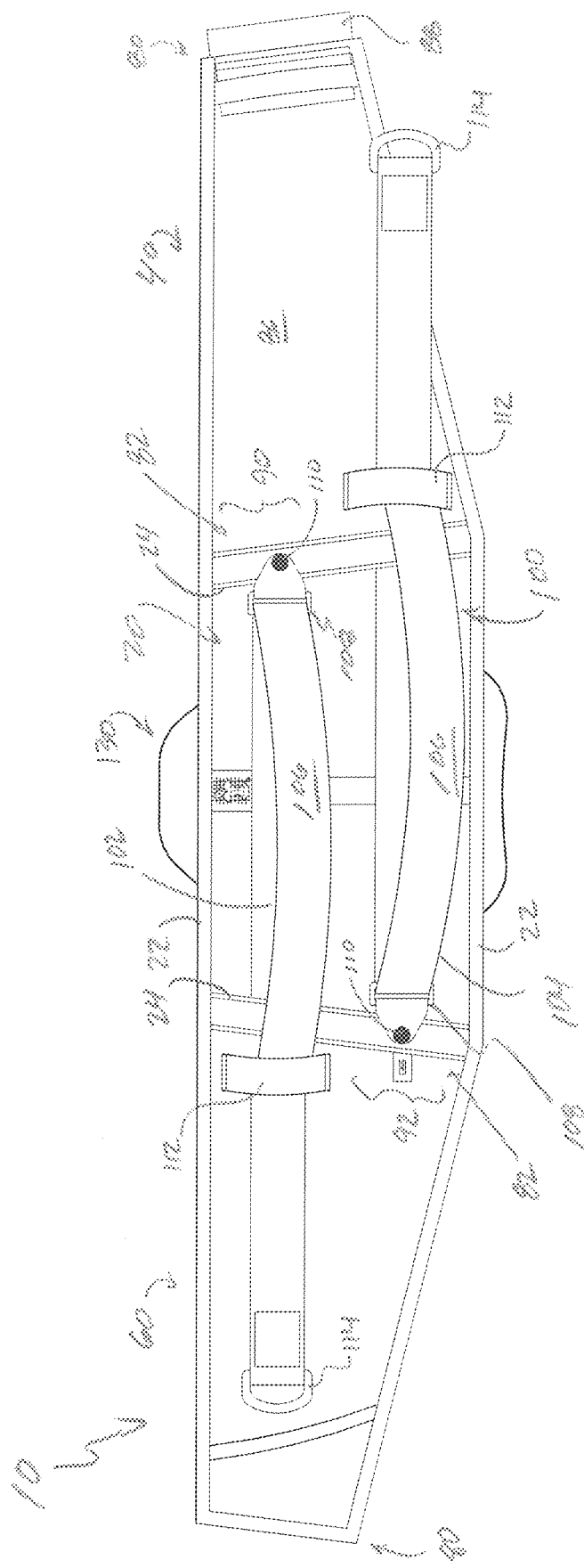
FIG. 2 depicts the lumbosacral wrap of FIG. 1, exterior view, fully extended.
Figure 3:
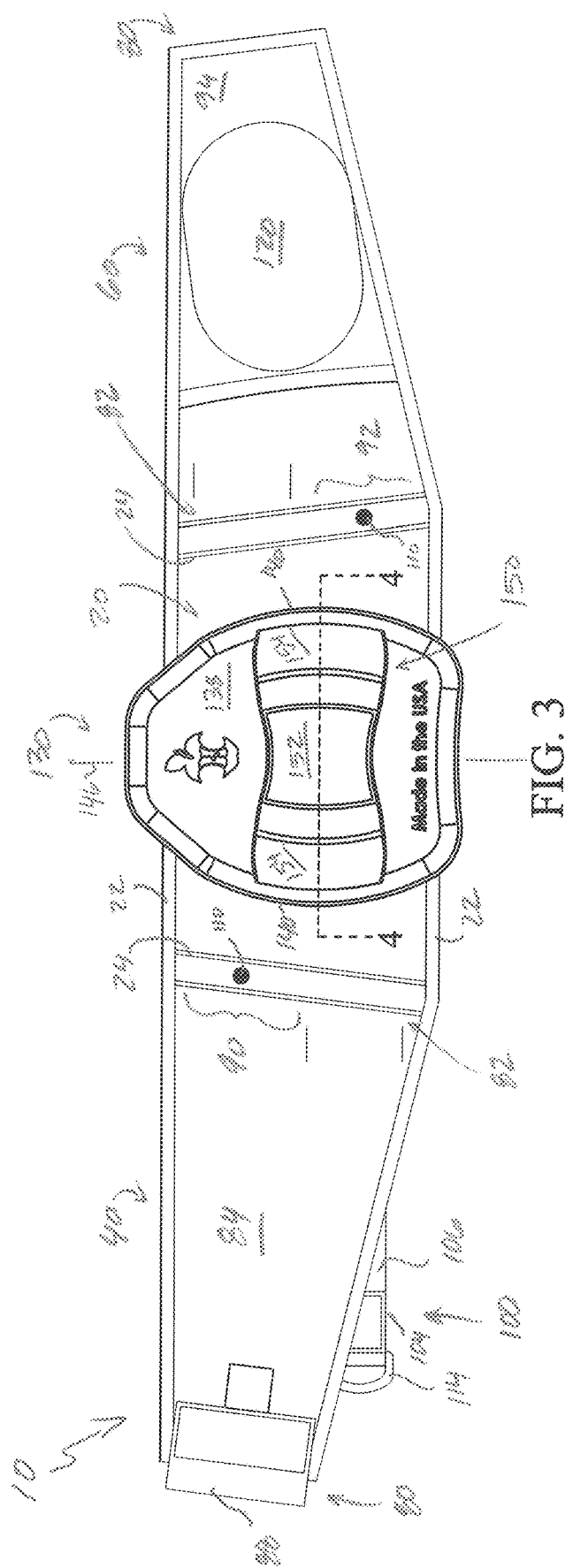
FIG. 3 depicts the lumbosacral wrap of FIG. 1, interior view, fully extended, a full "front" elevation view of an advantageous, non-limiting posterior pad thereby provided.
Figure 4:
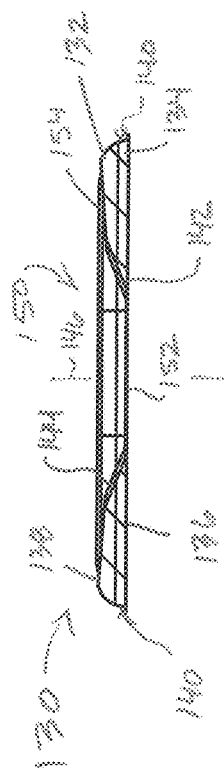
FIG. 4 depicts a sectional view of the posterior pad of FIG. 2 about line 4-4 thereof, namely, through a horizontal centerline of the wireless TENS unit supported thereby.

As a preliminary matter, FIGS. 1-3 depict a preferred, non-limiting embodiment of the contemplated lumbosacral wrap equipped with an improved posterior/lumbar pad, particulars as to one pad embodiment depicted in FIGS. 3 & 4 and particulars as to another pad embodiment depicted in FIGS. 5 & 6. In advance of further disclosure, alternate forms are contemplated for each/either of the wrap per se and the posterior pad. It should be appreciated that notionally, via disclosed/depicted and/or functionally equivalent structures, and their interrelationship(s), an advantageous and desirable wrap is provided, namely, one practically combining support and select user compression with stimulation as circumstances warrant.

With general reference to FIGS. 1-3, a non-limiting, advantageous lumbosacral wrap 10 shown in two configurations (i.e., FIG. 1 versus FIGS. 2 & 3) and two views (i.e., FIG. 2 & FIG. 3). Generally, the wrap is fairly characterized by wrap forming panels, closure means in furtherance of securing opposing wrap end portions to each other about a wearer, and compression adjustment means in furtherance of selectively cinching the wrap to compressingly support the lumbosacral anatomy. The wrap may be optionally and advantageously, but not necessarily, equipped with one or more complementary structures (i.e., reinforcing members) for specific support/compression as circumstances necessitate. Moreover, via adaptation of the wrap per se, or alternately and advantageously, adaptation of a lumbar reinforcement member, either of the wrap or reinforcement member may be selectively, quickly and easily equipped with a wireless transcutaneous electrical nerve stimulation (TENS) device.

Wrap 10, as shown, includes a lumbosacral panel 20 characterized by opposing longitudinal margins 22 and opposing lateral margins 24. As will be later taken up, lateral margins 24 preferably, but not necessarily comprise or function as stays, and generally delimit an interface for and between the panels of the wrap. A first bilateral panel 40 extends from a first margin of opposing lateral margins 24 of lumbosacral panel 20, and a second bilateral panel 60 extends from a second margin of opposing lateral margins 24 of lumbosacral panel 20.

Each of the bilateral panels 40, 60 are fairly characterized as having opposing first (e.g., "free") 80 and second 82 end portions, and first (e.g., interior) 84 and second (e.g., exterior) 86 surfaces. Second end potions 82 of bilateral panels 40, 60 are generally bounded by lateral margins 24 of lumbosacral panel 20. First free end portions 80 of bilateral panels 40, 60 are adapted in known ways to effectuate select reversible union in furtherance of wrap closure about a user. For example, and without limitation, an interior surface 84 of free end portion 80 of one bilateral panel (e.g., first panel 40 as shown) is equipped with a closure tab 88 characterized by a component of a hook-and-loop fastening system (e.g., hooks), with an exterior surface 86 of free end portion 80 of the other bilateral panel (e.g., second panel 82 as shown) comprised of a cooperative hook-and-loop fastening system component (e.g., loops). Advantageously, exterior surfaces 86 of bilateral panels 40, 60 include or comprise a component of a hook-and-loop fastening system (e.g., loops), with interior surfaces 84 (i.e., user contacting surfaces) thereof advantageously characterized by a moisture wicking material, e.g., polyester, as is generally known.

Second end portions 82 of bilateral panels 40, 60 are characterized by second end segments, for instance first and second, or to facilitate further discussion, upper (i.e., lumbar) 90 and lower (sacral) 92 end segments as shown. Opposing upper/lumbar second end segments 90 and opposing lower/sacral second end segments 92 of each second end portion 82 of each bilateral panel 40, 60, at least indirectly, are operatively united via elements or portions of a binding system such that independent and focused user adjustment, i.e., compression adjustment, in relation to either or both of the lumbar or sacral spinal segments is permitted.

A binding system 100 advantageously operatively unites first 40 and second 60 bilateral wrap panels in furtherance of tensioningly adjusting the wrap. Binding system 100 is generally and fairly characterized by cinching assemblies, namely, first (e.g., "upper" lumbar) 102 and second (e.g., "lower" sacral) 104 cinching assemblies as shown, each characterized by a strap 106 and an anchored keeper 108. Each strap 106 extends from either of upper/lumbar 90 or lower/sacral segment 92 of second end portion 82 of the respective bilateral panel 40, 60 to which it is affixed or otherwise united. Strap 106 traverses lumbosacral panel 20 for passage through keeper 108 which is pivotably supported at an opposite upper/lumbar or lower/sacral segment of second end portion of the opposing bilateral panel, via, as shown, a rivet 110. Straps 106 pass through keeper 108 and further extend in a direction opposite whence they came for passage through a further fixed keeper (i.e., an upper/lumbar or a lower/sacral fixed keeper 112) supported interior of a margin proximal to either of upper/lumbar 90 or lower/sacral segment 92 of second end portion 82 of the opposing bilateral panel as the case may be. A free end of straps 106 are characterized by a d-ring 114 or the like to aid tension application and a component of a hook and loop fastening system to enable reversible union of the free end portion of the strap to the exterior surface of the bilateral panels.

With continued general reference to FIGS. 1 & 2, and select reference to FIGS. 3 & 4 on one hand and FIGS. 5 & 6 on the other hand, provisions are advantageously made for selectively equipping the wrap with either or both of an anterior panel 120 or a posterior/lumbar pad 130. As to the former, its is suitably and conveniently received within an interior pocket 94 of a bilateral panel, e.g., second bilateral panel 60 as shown (FIG. 3). As to the latter, it is suitably and conveniently affixed or otherwise conventionally supported by lumbosacral panel 20, as by, for instance, elements of a hook and loop fastening system, more particularly, posterior/lumbar pad 130 is supportable by lumbosacral panel 20 intermediate opposing lateral margins 24 thereof.

While numerous posterior/lumbar pad constructs are known and believed adaptable for the functionality contemplated, two non-limiting pad styles are depicted for the sake of discussion, namely, a "full" pad (FIG. 3) and a "short" pad (FIG. 5). Advantageously, pads 130 are characterized by a dual density construct, namely, a layer of resilient padding 132 is supported by a rigid yet axially flexible substrate 134.

With particular reference to FIGS. 3-6, posterior pad 130 (FIG. 3, FIG. 5) has a panel engaging surface (rigid) 136, a user engaging surface (resilient) 138, and opposing sides 140, user engaging surface 138 of posterior pad 130 characterized by an adaptation, e.g., a cavity 142 extending between opposing sides 140 of posterior pad 130, to permit operative union with a wireless, remotely controllable (TENS) device 150. In the context of the contemplated adaptation, e.g., and without limitation, a cavity, recess, select contouring of the user engaging surface of the posterior pad, the wireless, remotely controllable TENS device is receiveable within, for example, the cavity of the user engaging surface of the pad in furtherance of supplementing support and compression of the lumbosacral spine with mobile pain relief. Notionally, and as is generally depicted, the contemplated combination delimits or defines a substantially flat surface for user engagement. Moreover, cavity 142, as shown, advantageously but not necessarily is delimited by sloping horizontal pad surfaces 144 outwardly extending from a vertical centerline 146 of the pad. The cavity may be a recess, or a through hole.

The wireless TENS unit is reversibly received in relation to the cavity, and advantageously, but not necessarily retained thereby via conventional means such as, but hardly limited to, elements of a hook and loop fastening system or adhesives. More particularly, a central housing 152 of the unit 150, from which extend flexible electrodes 154, is adapted to facilitate a reversible affixation directly to pad 130, or in the case of a cavity characterized by a through hole, affixation indirectly to the pad as by a strap or other housing receiving member traversing the through hole and generally supported by/upon the panel engaging surface thereof. A contemplated and exemplary wireless TENS unit is the WiTouch by Hollywog, Chattanooga, Tenn., USA (http://www.hollvwoa.com/products/witouch-pro), the published specifications thereof incorporated herein by reference.

Finally, since the structures of the assemblies/mechanisms disclosed herein may be embodied in other specific forms without departing from the spirit or general characteristics thereof, some of which forms have been indicated, the embodiments described and depicted herein/with are to be considered in all respects illustrative and not restrictive. Accordingly, the scope of the one or more disclosed inventions is/are as defined in the language of the appended claims, and includes not insubstantial equivalents thereto.

That which is claimed:

1. A lumbosacral wrap comprising:
   a lumbosacral panel characterized by opposing longitudinal margins and opposing lateral margins;
   a first bilateral panel connected with and extending from a first margin of said opposing lateral margins of said lumbosacral panel, said first bilateral panel having interior and exterior surfaces and a free end portion opposite said first margin of said opposing lateral margins of said lumbosacral panel;
   a second bilateral panel connected with and extending from a second margin of said opposing lateral margins of said lumbosacral panel, said second bilateral panel having interior and exterior surfaces and a free end portion opposite said first margin of said opposing lateral margins of said lumbosacral panel;
   a posterior pad supportable by said lumbosacral panel, intermediate said opposing lateral margins thereof, said posterior pad having a panel engaging surface, a user engaging surface, and opposing sides, said user engaging surface of said posterior pad characterized by a cavity extending between said opposing sides of said posterior pad;
   an upper cinching assembly anchored to the lumbosacral panel at the first margin and at the second margin, and extending with the first bilateral panel;
   a lower cinching assembly anchored to the lumbosacral panel at the second margin and at the first margin, and extending with the second bilateral panel;
   wherein each of the opposing lateral margins define an interface between the lumbosacral panel and the first bilateral panel and an interface between the lumbosacral panel and the second bilateral panel;
   wherein the upper cinching assembly includes a first keeper anchored to the lumbosacral panel closer to the second margin than the first margin; and
   wherein the first keeper is pivotably coupled to the lumbosacral panel.

2. The wrap of claim 1, including a wireless transcutaneous electrical nerve stimulation device receivable within the cavity of said user engaging surface of the posterior pad in furtherance of supplementing support and compression of a lumbosacral spine with mobile treatment; and
   wherein the wireless transcutaneous electrical nerve stimulation device is configured to extend and form a portion of the user engaging surface, and to directly engage a user.

3. The wrap of claim 2, wherein the wireless transcutcutaneous electrical nerve stimulation device is retained within the cavity via an element of a hook and loop fastening system directly connected to the wireless transcutaneous electrical nerve stimulation device.

4. The wrap of claim 2, wherein the wireless transcutaneous electrical nerve stimulation device is characterized by a housing and electrodes extending therefrom, the wireless transcutaneous electrical nerve stimulation device received within the cavity so as to define a substantially flat user engagement surface for the posterior pad.

5. The wrap of claim 1 wherein said cavity comprises a through hole in said user engaging surface of said posterior pad.

6. The wrap of claim 1 wherein said posterior pad is characterized by a dual density.

7. The wrap of claim 1 wherein said posterior pad comprises a layer of resilient padding supported by a substrate.

8. The wrap of claim 1, wherein an anchor for the upper cinching assembly is offset vertically from an anchor of the lower cinching assembly.

9. The wrap of claim 1, wherein the upper cinching assembly includes a first strap anchored to the lumbosacral panel and passing through the first keeper.

10. The wrap of claim 1, including a fixed keeper coupled to the first bilateral panel, the fixed keeper configured to keep the first strap.

11. The wrap of claim 1, wherein the upper cinching assembly includes a upper cinching strap anchored to the first margin, the upper cinching strap configured to extend from the first margin across the lumbosacral panel toward the second margin, and to extend away from the second margin across the lumbosacral panel and with the first bilateral panel; and
    wherein the lower cinching assembly includes a lower cinching strap anchored to the lumbosacral panel at the second margin, the lower cinching strap configured to extend from the second margin across the lumbosacral panel toward the first margin, and to extend away from the first margin across the lumbosacral panel and with the second bilateral panel.

12. A lumbosacral wrap comprising:
    a lumbosacral panel characterized by opposing longitudinal margins and opposing lateral margins;
    a first bilateral panel connected with and extending from a first margin of said opposing lateral margins of said lumbosacral panel, said first bilateral panel having interior and exterior surfaces and a free end portion opposite said first margin of said opposing lateral margins of said lumbosacral panel;
a second bilateral panel connected with and extending from a second margin of said opposing lateral margins of said lumbosacral panel, said second bilateral panel having interior and exterior surfaces and a free end portion opposite said first margin of said opposing lateral margins of said lumbosacral panel;
a posterior pad supportable by said lumbosacral panel, intermediate said opposing lateral margins thereof, said posterior pad having a panel engaging surface, a user engaging surface, and opposing sides, said user engaging surface of said posterior pad characterized by a cavity extending between said opposing sides of said posterior pad;
an upper cinching strap anchored to the lumbosacral panel closer at the first margin, the upper cinching strap configured to extend from the first margin across the lumbosacral panel to an anchor at the second margin, and to extend away from the second margin across the lumbosacral panel and with the first bilateral panel;
a lower cinching strap anchored to the lumbosacral panel closer at the second margin, the lower cinching strap configured to extend from the second margin across the lumbosacral panel toward an anchor at the first margin, and to extend away from the first margin across the lumbosacral panel and with the second bilateral panel;
wherein the anchor at the second margin includes a first keeper pivotably anchored to the second margin and configured to change a wrap direction of the upper cinching strap; and
wherein the anchor at the first margin includes a second keeper pivotably anchored to the first margin and configured to change a wrap direction of the lower cinching strap.

13. The lumbosacral wrap of claim 12, including a wireless transcutaneous electrical nerve stimulation device receivable within the cavity of said user engaging surface of the posterior pad in furtherance of supplementing support and compression of a lumbosacral spine with mobile treatment; and
wherein the wireless transcutaneous electrical nerve stimulation device is configured to extend and form a portion of the user engaging surface, and to directly engage a user.

14. The lumbosacral wrap of claim 13, wherein the wireless transcutaneous electrical nerve stimulation device is retained within the cavity via an element of a hook and loop fastening system directly connected to the wireless transcutaneous electrical nerve stimulation device.

15. The lumbosacral wrap of claim 13, wherein the wireless transcutaneous electrical nerve stimulation device is characterized by a housing and electrodes extending therefrom, the wireless transcutaneous electrical nerve stimulation device received within the cavity so as to define a substantially flat user engagement surface for the posterior pad.

16. The lumbosacral wrap of claim 12, wherein the opposing lateral margins are stays.

17. A lumbosacral wrap comprising:
a lumbosacral panel characterized by opposing longitudinal margins and opposing lateral margins;
a first bilateral panel connected with and extending from a first margin of said opposing lateral margins of said lumbosacral panel, said first bilateral panel having interior and exterior surfaces and a free end portion opposite said first margin of said opposing lateral margins of said lumbosacral panel;
a second bilateral panel connected with and extending from a second margin of said opposing lateral margins of said lumbosacral panel, said second bilateral panel having interior and exterior surfaces and a free end portion opposite said first margin of said opposing lateral margins of said lumbosacral panel;
a posterior pad supportable by said lumbosacral panel, intermediate said opposing lateral margins thereof, said posterior pad having a panel engaging surface, a user engaging surface, and opposing sides, said user engaging surface of said posterior pad characterized by a cavity extending between said opposing sides of said posterior pad;
an upper cinching assembly anchored to the lumbosacral panel closer to the first margin than the second margin and extending with the first bilateral panel;
a lower cinching assembly anchored to the lumbosacral panel closer to the second margin than the first margin and extending with the second bilateral panel; and
wherein said posterior pad comprises a layer of resilient padding supported by a rigid, axial flexible substrate.

18. The lumbosacral wrap of claim 17, including a wireless transcutaneous electrical nerve stimulation device receivable within the cavity.

19. The lumbosacral wrap of claim 18, wherein the wireless transcutaneous electrical nerve stimulation device is retained within the cavity via an element of a hook and loop fastening system.

20. The lumbosacral wrap of claim 17, wherein the upper cinching assembly includes a first keeper anchored to the lumbosacral panel closer to the second margin than the first margin.

* * * * *